(12) United States Patent
Shuku et al.

(10) Patent No.: US 6,355,263 B1
(45) Date of Patent: Mar. 12, 2002

(54) CLOTHING PROMOTING METABOLISM OF KERATIN LAYER

(75) Inventors: Kiyokazu Shuku, Shiki-gun; Hiromi Kashihara, Kashihara, both of (JP)

(73) Assignee: Okamoto Corporation (JP)

( * ) Notice: Subject to any disclaimer, the term of this patent is extended or adjusted under 35 U.S.C. 154(b) by 0 days.

(21) Appl. No.: 09/499,780

(22) Filed: Feb. 8, 2000

(30) Foreign Application Priority Data

Feb. 8, 1999 (JP) .......................................... 11-070697

(51) Int. Cl.$^7$ .......................... A01N 25/34; A41B 9/00; A41B 11/04
(52) U.S. Cl. ............................... 424/402; 2/400; 2/409
(58) Field of Search ............................. 424/402; 2/409, 2/400

(56) References Cited

U.S. PATENT DOCUMENTS 5,232,769 A * 8/1993 Yamato et al. .............. 424/402

\* cited by examiner

Primary Examiner—Thurman K. Page
Assistant Examiner—Blessing Fubara
(74) Attorney, Agent, or Firm—Morrison Law Firm

(57) ABSTRACT

A clothing with effects on the reduction of skin dryness, skin roughness, wrinkle and spot is provided, together with a method for attaching a microcapsule. The metabolism of keratin layer is promoted by using a clothing prepared by attaching to the fiber, a microcapsule containing and sealing therein at least 10% by weight of at least one α-hydroxy acid. Chitosan is used as a crosslinking agent. The microcapsule and chitosan are given within a range of from about 4:1 to about 1:6 in weight ratio. The total amount of the chitosan and the microcapsule occupies from about 0.1 to about 15% of the fiber weight at a dry state.

6 Claims, 5 Drawing Sheets

(3 of 5 Drawing Sheet(s) Filed in Color)

CLOTHING PROMOTING METABOLISM OF KERATIN LAYER

BACKGROUND OF THE INVENTION

The present invention relates to a clothing with an action promoting the metabolism of keratin layer and a method for attaching a preferable microcapsule.

Cells composing epidermis are keratinized over maturity because of the accumulation of keratin, so that keratin layer is formed on the surface of skin. Keratin layer is mostly composed of scaly dead cells but is responsible for such an important role for the protection of skin from outside by retaining moisture on skin.

When gets old, a keratin layer is peeled off. Then, a fresh keratin layer is formed on the portion. Bare skin can be retained at a good state by such smooth promotion of the metabolism of keratin layer. When the metabolism of keratin layer is deteriorated due to factors such as aging, stress, nutritional imbalance, and poor care, however, skin gets dry and puffy, causing, for example rough skin, wrinkle and spot.

So as to reduce skin dryness, skin roughness, wrinkle and spot, accordingly, it is most effective to ameliorate the state of keratin hypertrophy involving old keratin layer remaining on skin for a long term and thereby promote the metabolism of keratin layer. So as to resume skin moisture and softness once reduced, further, care is preferably taken on skin so that the metabolism of keratin layer can be promoted and moisture is appropriately retained on skin.

Alternatively, it has been known conventionally that α-hydroxy acids, for example lactic acid, have an action to loosen and soften the binding of old keratin layer densely overlaid together. For example, α-hydroxy acids at a high concentration of about 5 to 20% by weight are used as keratolytic agent for the treatment of callus, verruca and corn and also used as skin peeling agent at beauty salon.

In recent years, additionally, a proposition has been made of a method comprising sealing in a microcapsule a physiologically active substance conventionally used in the forms of external dermal agent and cosmetics and attaching the microcapsule to the fiber of clothing. Such clothing with the physiologically active substance-containing microcapsule attached thereto is intended to perform skin care while the clothing is continuously worn during day-time hours, although skin care has essentially been carried out, mainly before bathing or sleeping by external dermal agents and cosmetics, conventionally.

As one example thereof, Japanese Patent No. 2562233 proposes a fiber structure comprising a microcapsule for fiber-processing agents and a structural fiber to which the microcapsule is attached with a silicone-based or urethane-based resin binder, wherein the microcapsule contains and seals therein at least one substance with an action improving dermal physiological state, as selected from the group consisting of ascorbic acids, tocopherols, sea weed extracts, antipruritics and analgesics and comprises a wall membrane of a synthetic polymer substance and wherein the particle size of the microcapsule is within a range of 2 to 40 μm and the wall membrane is 0.3 to 4 μm thick and the content of the wall membrane is 3 to 60% by weight on a microcapsule weight basis and wherein the weight ratio of the microcapsule and the binder is within a range of 10:1 to 1:5 and the total amount of both the attached microcapsule and binder occupies 0.3 to 15% of the fiber weight in the attached portion.

As to the method for attaching such microcapsule to the fiber of clothing, furthermore, various methods have been proposed conventionally, where the binder types to be added and reaction conditions have been devised and modified. For example, Japanese Patent Publication 80121/1992 proposes, as one example of microcapsule with fragrance, a method for producing a stocking with fragrance, comprising charging a stocking in a process bath containing a microcapsule with fragrance and a silicone-based coating agent in mixture at a weight ratio of 1:1 to 1:2, and subjecting the stocking at a thermal process at 20 to 60° C. while the hydrogen ion concentration is preset and retained within a range of 4 to 6 in the process bath by using a buffer.

The method for attaching microcapsule as described in the Japanese Patent Publication No. 80121/1992, for example, specifies the conditions such as hydrogen ion concentration and reaction temperature for enhancing the binding between the microcapsule and the coating agent and between the microcapsule coating agent and the fabric, so as to suppress as much as possible the dissociation of the microcapsule after the attachment, due to washing. However, the method does not pay any consideration to the elevation of the attachment ratio of the microcapsule during adsorption reaction.

According to the method, thus, the amount of the microcapsule charged in a process bath is not equal to the amount of the microcapsule attached to the fiber and the attachment ratio thereof varies with a deviation, depending on the process conditions. From the standpoint of quality control, the method is problematic in that the amount of the microcapsule attached to panty stocking can hardly be retained constant.

Generally, a slight error in the amount of the microcapsule attached is not so problematic in case of a clothing attached with such a fragrance-containing microcapsule as described above. However, it is needless to say that a more strict quality control is demanded for a clothing attached with a microcapsule containing and sealing therein a substance with a physiological action on skin.

Although α-hydroxy acids as natural acids contained in fruit and the like are highly safe, particularly, caution should be taken on the concentration thereof for use. More specifically, some of α-hydroxy acids have been used conventionally at high concentrations of about 5 to 20% by weight as keratolytic agents and peeling agents. For the purpose of gently promoting the metabolism of keratin layer, essentially, α-hydroxy acids are directly coated within a range of 1.5 to 3.0% by weight. At a concentration above the range, human skin sensitive to α-hydroxy acids is potentially irritated.

Furthermore, because the microcapsule described in for example the Japanese Patent No. 2562233 is a decomposable microcapsule containing and sealing therein as the principal ingredient, a thermoset resin for example formalin resin or polyester resin, some of such microcapsules are decomposed under exposure to pressure and friction during fiber processing, prior to product shipping, so that the amount of the microcapsule still holding the effect is decreased by the time when a user wears it, which is problematic from the respect of quality control.

Additionally, the decomposable microcapsule is of a preferable membrane thickness specifically conditioned for gradual decomposition of the microcapsule over wearing. Because the microcapsule is practically at a high decomposition probability at an early stage of use where a larger volume of the microcapsule is attached to portions readily exposed to pressure or friction, the physiologically active substance in the microcapsule is released more at such early stage of use, disadvantageously.

For containing a physiologically active substance such as antipruritic, for which a relatively rapid efficacy is demanded, a decomposable microcapsule can be used, satisfactorily. Because the action of α-hydroxy acids to promote the metabolism of keratin layer requires about one month until the action is exerted effectively as remedies of dry skin and rough skin, the effect preferable can hardly be recovered by using a decomposable microcapsule with a higher release level at an early stage of use.

In such circumstances with the conventional problems, the invention has been achieved. It is a main purpose of the invention to provide a preferable clothing exerting an action to promote the metabolism of keratin layer and overcoming the quality-control problems, and a method for attaching such microcapsule to fiber.

OBJECTS AND SUMMARY OF THE INVENTION

It is an object of the present invention to provide a clothing which overcomes the foregoing problems.

It is a further object of the present invention to provide a clothing having an action promoting the metabolism of keratin layer.

It is another object of the present invention to provide a method for attaching a microcapsule to fiber to give a clothing having an action promoting the metabolism of keratin layer.

So as to attain the purpose, the clothing promoting the metabolism of keratin layer in accordance with the invention is prepared by attaching to a fiber a microcapsule containing and sealing therein 10% by weight or more of one or plural ones in mixture as selected from α-hydroxy acids by using chitosan as crosslinking agent, wherein the clothing is composed such that the microcapsule and chitosan are at a weight ratio within a range of from about 4:1 to about 1:6, and the total amount of both of the two attached occupies from about 0.1 to about 15% of the fiber weight at dry state in the attached portion. Additionally, inorganic porous materials are preferably used as the wall material of the microcapsule.

The method for attaching the microcapsule in accordance with the invention comprises pouring and immersing a dispersion solution containing from about 4 to about 20% by weight of the microcapsule and at least 4 to about 30% by weight of chitosan and being adjusted of the initial pH within a range of from about 6.0 to about 7.0 in a process bath charged with a fabric, for immersion, thereafter raising the temperature of the process bath charged with the dispersion solution up to from about 40 to about 55° C. as the upper limit and retaining the upper limit temperature to cany out absolute absorption process.

Briefly stated, the present invention relates to a clothing with effects on the reduction of skin dryness, skin roughness, wrinkle and spot, together with a method for attaching a microcapsule. The metabolism of keratin layer is promoted by using a clothing prepared by attaching to the fiber, a microcapsule containing and sealing therein at least 10% by weight of at least one α-hydroxy acid. Chitosan is used as a crosslinking agent. The microcapsule and chitosan are given within a range of from about 4:1 to about 1:6 in weight ratio. The total amount of the chitosan and the microcapsule occupies from about 0.1 to about 15% of the fiber weight at a dry state.

According to an embodiment of the present invention, there is provided a clothing comprising: a fiber having a microcapsule containing and sealing therein at least about 10% by weight of at least one α-hydroxy acid, by using chitosan as a crosslinking agent thereby improving the state of bare skin through the promotion of the metabolism of keratin layer; the microcapsule and the chitosan being present within a range of from about 4:1 to about 1:6 in weight ratio; and a total amount of the microcapsule and the chitosan occupying from about 0.1 to about 15% of the fiber weight at a dry state.

According to another embodiment of the present invention, there is provided a method for attaching a microcapsule to a fiber, comprising: forming a dispersion solution containing from about 4 to about 20% by weight of the microcapsule and at least 4 to about 30% by weight of chitosan; adjusting an initial pH of the dispersion within a range of from about 6.0 to about 7.0; immersing the fabric into a process bath; pouring the dispersion in the process bath; adjusting the temperature of the process bath charged with the dispersion solution up to a range from about 40 to about 55° C.; and maintaining the temperature to carry out absolute absorption of the microcapsule onto the fiber.

The above, and other objects, features and advantages of the present invention will become apparent from the following description read in conjunction with the accompanying drawings, in which like reference numerals designate the same elements.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DETAILED DESCRIPTION OF THE INVENTION

The present inventors have made investigations with energetic efforts. The inventors have found that by pouring and immersing a dispersion solution containing 4 to 20% by weight of the microcapsule and at least 4 to 30% by weight of chitosan in a process bath charged with a fabric after refinery, dyeing and fix processes, for immersion, thereafter raising the temperature of the process bath charged with the dispersion solution up to from about 40 to about 55° C. as the upper limit and retaining the upper limit temperature to carry out absolute absorption process, the attachment ratio of the microcapsule to the fiber is prominently elevated so that the microcapsule is absolutely absorbed at an extent such that no remaining microcapsule is present in the dispersion solution after these processes.

It is just deduced that the mechanism of the absolute absorption using chitosan as crosslinking agent is ascribed to the aggregation potency of chitosan involved in the binding between chitosan and the microcapsule and to the ionic binding between cationic chitosan and anion-charged fiber surface after refinery, dye and fix processes. The ionic binding works for the binding between the chitosan microcapsule and the fiber. Possibly, these aggregation potency and ionic binding together bring about a synergistic effect. The inventors additionally have found that absolute absorption can be effected greatly when the initial pH condition of the preferable dispersion solution is specified. Thus, the method for attaching the microcapsule in accordance with the invention has been achieved.

In other words, in case that the initial pH of the dispersion solution is more than 7.0, absolute absorption is initiated, just immediately when the dispersion solution is poured in a process bath charged with a fabric, for immersion. Consequently, no good outcome can be yielded. In case that the initial pH of the dispersion solution is less than 6.0, alternatively, absolute absorption can never be completed, even when the process bath with the dispersion solution poured therein is raised up to 55° C. for the processing for a considerable period of time. According to the method for attaching the microcapsule in accordance with the invention, hence, the initial pH of the dispersion solution is preset within a range of from about 6.0 to about 7.0.

For the clothing promoting the metabolism of keratin layer in accordance with the invention, α-hydroxy acids are used at an amount within a range where an action to promote the metabolism of keratin layer can be exerted with no potential side effects. For the clothing of the invention, therefore, the amount of α-hydroxy acids to be used is adjusted by both the concentration of α-hydroxy acids in the microcapsule and the amount of the microcapsule attached to the fiber, in such a manner that the concentration of α-hydroxy acids in the microcapsule is at least 10% by weight or more; the total amount of both the microcapsule and chitosan is within a range of 0.1 to 15% of the fiber weight at dry state in the attached portion.

The term "hydroxy acids" refers to organic compounds with both a carboxyl group —COO and a hydroxyl group —OH within the molecule. The term "α-hydroxy acids" represents the generic name of compounds where hydroxyl group is bonded to a base carbon atom bonded with carboxyl group. Examples of α-hydroxyl groups include lactic acid, citric acid, glycolic acid, malic acid and tartaric acid. For the clothing of the invention, use is made of a single α-hydroxy acid or plural α-hydroxy acids in mixture, as appropriately selected from these α-hydroxy acids.

So as to improve the absorption ratio of the microcapsule during absorption reaction as much as possible for the clothing of the invention, chitosan is used as crosslinking agent and the weight ratio of the microcapsule containing and sealing therein α-hydroxy acids and chitosan is preset within a range of from about 4:1 to about 1:6. Because the chitosan to be added as crosslinking agent is antibacterial, the clothing of the invention has an antibacterial action as well.

In order that the α-hydroxy acids contained and sealed therein are released continuously at a constant ratio, the microcapsule of a wall material comprising an inorganic porous material is preferably used. In this case, the microcapsule comprises any component, with no specific limitation. For example, appropriate are alkali earth metals, for example calcium carbonate, barium carbonate and magnesium carbonate; alkali earth silicates, for example potassium silicate, barium silicate and magnesium silicate; metal oxides, for example silica, cobalt oxide and nickel oxide; and metal carbonate salts, for example cobalt carbonate and nickel carbonate.

As to porosity, furthermore, a microcapsule with a specific surface area within a range of from about 100 to about 800 $m^2/g$ and a pore diameter within a range of from about 20 to about 600 angstroms on the particle surface are appropriate.

So as to enhance the binding between the microcapsule and the fiber in the clothing of the invention, preferably, an urethane-based resin binder is added. Then, the weight ratio of the microcapsule and the urethane-based resin binder is preset within a range of from about 4:1 to about 1:5. In such manner, the durability against washing can be enhanced after the start of wearing.

So as to resume reduced skin moisture and softness together with the exertion of the action for promoting the metabolism of keratin layer, the clothing of the invention is preferably composed by attaching to the fiber either one or both of the microcapsule containing and sealing therein one or more moisturizing agents selected from cucumber extract, squalene, mugwort extract and trehalose, along with α-hydroxy acids and the microcapsule containing and sealing therein the moisturizing agents as the principal ingredient with no blend of α-hydroxy acids, so that the moisture content of skin can be retained at a good state; then, the ratio of α-hydroxy acids and the moisturizing agents is overall preset within a range of from about 4:1 to about 1:3, so that the moisture content of skin can be kept at a good state.

Because the clothing of the invention is of any type as long as the fabric area attached with the microcapsule on the fiber thereof can directly contact to bare skin to be treated, the type of the clothing includes, but with no limitation, for example socks, underwear, shirts, sleeping wear, leotard, spats, tights, scarf, gloves and supporter.

From the respect of the advantage of adhesion to bare skin, it can be said that stockings are the most appropriate clothing for the application of the invention. Herein, the term stockings is the generic name of overknee stocking of a leg length over knee, full-length stocking around the root of thigh, and panty stocking with party portion and stocking portion in integration. As the raw material of stockings, additionally, any of synthetic fibers such as nylon and polyester or natural fibers such as cotton can satisfactorily be selected, with no limitation.

The clothing promoting the metabolism of keratin layer and the method for attaching the microcapsule in accordance with the invention are described with reference to examples. An example of panty stocking as one application of the invention is disclosed hereinbelow, but the clothing and the method for attaching the microcapsule in accordance with the invention are not limited to the example.

Panty Stockings

Panty stockings of the following specification were used below in Examples 1 to 3 and Comparative Examples 1 and 2.

Panty part: cross-knitted with 30/30 filament textured yarn and 50/17 woolly nylon.

Leg part: zokki type of 15/12-7 single covered yarn

Nylon yarn: Miracosmo (under trade name; manufactured by Toray, Co.)

Polyurethane yarn: Operon (under trade name; manufactured by Toray Dupont Ltd.).

Microcapsule

The microcapsule of the following specification was used as the microcapsule containing and sealing therein α-hydroxy acids and moisturizing agents in Examples 1 to 3 and Comparative Example 2.

Principal component of wall material: alkali earth metal carbonate salts (calcium carbonate, barium carbonate, magnesium carbonate).

Shape and morphology: spherical, porous hollow.

Particle size range: 0.5 to 4.0 μm

Average particle size: 2.2 μm

Specific surface area: 545 m²/g

Surface pore range: 50 to 150 angstroms

The substances contained and sealed in the microcapsule are described below in 1 and 2. Glycerin, to be added as solvent in microcapsule 1, containing α-hydroxy acids as the principal ingredient also functions as moisturizing agent.

1. Microcapsule containing and sealing therein α-hydroxy acids as principal ingredient

| α-Hydroxy acids: | |
| --- | --- |
| lactic acid | 23.5% by weight |
| citric acid | 5.0% by weight |
| glycolic acid | 2.5% by weight |
| malic acid | 2.5% by weight |
| tartaric acid | 0.1% by weight |
| other acids | |
| pyrrolidonecarboxylic acid | 5.0% by weight |
| pyruvic acid | 0.2% by weight |
| Solvent: | |
| water | 55.2% by weight |
| glycerin | 6.0% by weight |

2. Microcapsule containing and sealing therein a moisturizing agent as principal agent

| Moisturizing agent: | |
| --- | --- |
| cucumber extract | 100.0% by weight |

EXAMPLE 1

In Example 1, the following steps are carried out. The addition of a softener at the step 2 serves for the purpose of improving the touch of the panty stocking. The steam process and hot-air drying process at the step 5 serve for the purpose of arranging panty stocking in good shape. The panty stocking recovered in Example 1 was formed with the microcapsule and chitosan at a weight ratio of 1:2, where the total amount of both of the two attached occupies 6% of the fiber weight at dry state in the attached portion.

Step 1

Figures 1, 1A:
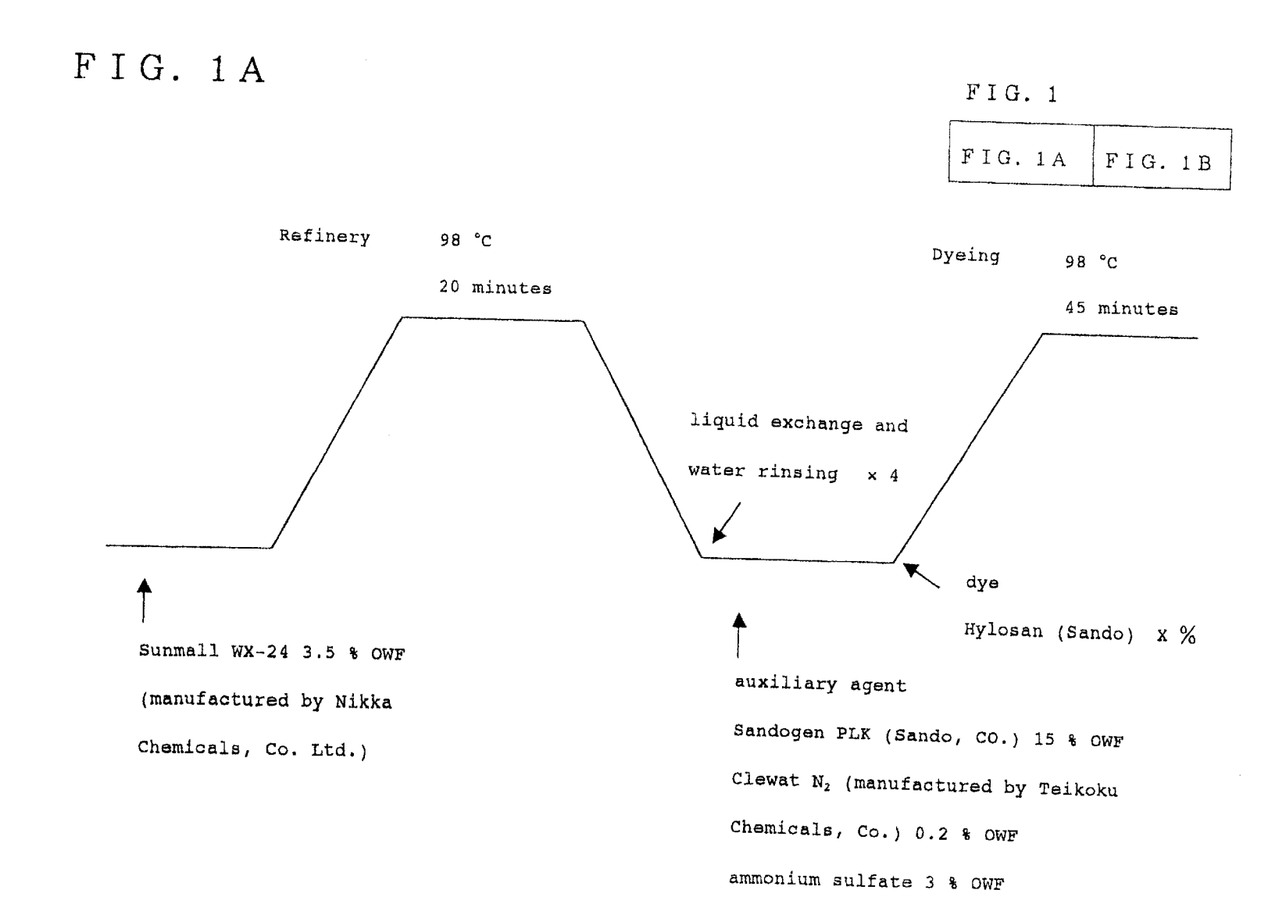
FIG. 1 shows a program chart depicting the standard dye process of panty stocking.
Figure 1B:
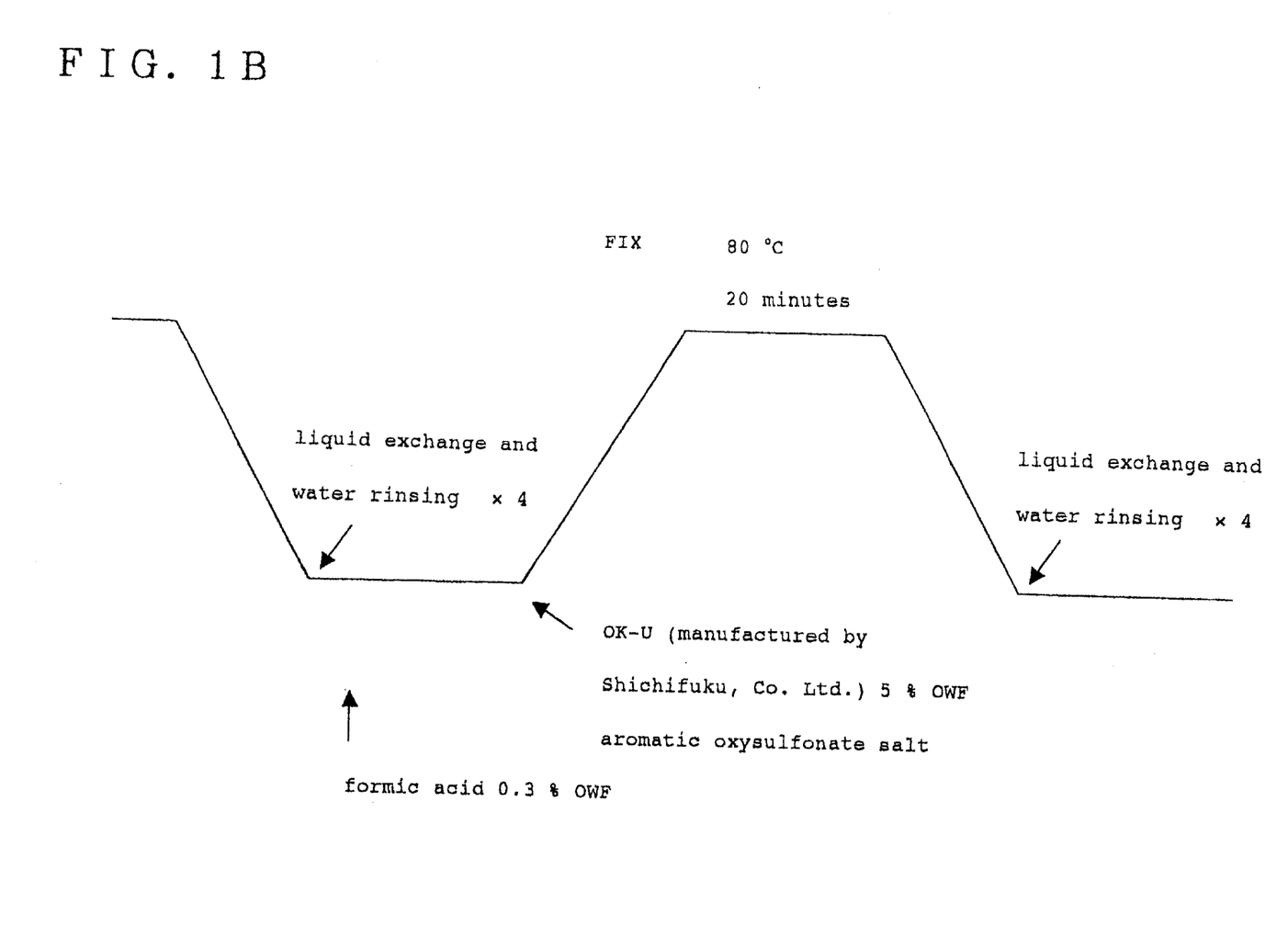

Following the standard steps shown in FIGS. 1A and 1B, 80 kg of the panty stocking is subjected to refinery, dyeing and fix processes by an Overmeyer dye machine and is then dehydrated with a dehydration centrifuge, which is thereafter charged in a drum dye machine.

Step 2

The dispersion solution is adjusted to satisfy the following conditions.

| Microcapsule containing and sealing therein α-hydroxy acids as the principal ingredient | 4.0% by weight |
| --- | --- |
| Chitosan: K-5 (under trade name; manufactured by Kurashiki Boseki) | 8.0% by weight |
| Softener: AQ-66 (under trade name; manufactured by Shichifuku Chemicals) | 4.0% by weight |
| Water | 84.0% by weight |
| Initial pH: 7.0 | |

Step 3

To a final ratio of 1:20 as the panty stocking: the dispersion solution in a bath, the dispersion solution is poured in the drum dye machine, for immersion.

Step 4

The temperature of the process bath with the dispersion solution poured therein is raised at a rate of 1° C./min to 40° C.; by retaining the temperature at 40° C., absolute absorption process is effected for 30 minutes.

Step 5

After the panty stocking is drawn out and thereafter dehydrated, the panty stocking is subjected to a steam process at a steam pressure of 1.1 kg/cm² for 20 seconds and is then dried in hot air at 110° C. for 25 seconds.

EXAMPLE 2

In the same manner as in Example 1 except for the modification of the steps 2 and 4 as follows, the panty stocking of Example 2 was recovered. Furthermore, the panty stocking recovered in Example 2 was given with the microcapsule and chitosan at a weight ratio of 1:3, where the total amount of both of the two attached occupies 8% of the fiber weight at dry state in the attached portion.

Step 2

The dispersion solution is adjusted to satisfy the following conditions.

| Microcapsule containing and sealing therein α-hydroxy acids as the principal ingredient | 5.0% by weight |
| --- | --- |
| Chitosan: K-5 (under trade name; manufactured by Kurashiki Boseki) | 10.0% by weight |
| Chitosan: SOK (under trade name; manufactured by Shichifuku Chemicals) | 5.0% by weight |
| Softener: AQ-66 (under trade name; manufactured by Shichifuku Chemicals) | 4.0% by weight |
| Water | 76.0% by weight |
| Initial pH: 6.8 | |

Step 4

The temperature of the process bath with the dispersion solution poured therein is raised at a rate of 1° C./min to 50° C.; by retaining the temperature at 50° C., absolute absorption process is effected for 30 minutes.

EXAMPLE 3

In the same manner as in Example 1 except for the modification of the steps 2 and 4 as follows, the panty stocking of Example 3 was recovered. In Example 3, furthermore, a binder comprising a heat-reactive water-soluble urethane with urethane backbone and block isocyanate group as the principal ingredient was added to the dispersion solution. Additionally, the panty stocking recovered in Example 3 was given with the microcapsule and chitosan at a weight ratio of 1:3.3, where the total amount of both of the two attached occupies 8.6% of the fiber weight at dry state in the attached portion.

Step 2

The dispersion solution is adjusted to satisfy the following conditions.

| | |
|---|---:|
| Microcapsule containing and sealing therein α-hydroxy acids as the principal ingredient | 5.0% by weight |
| Microcapsule containing and sealing therein the moisturizing agent as the principal ingredient | 1.0% by weight |
| Chitosan: SOK (under trade name; manufactured by Shichifuku Chemicals) | 20.0% by weight |
| Binder: NF-168N (under trade name; manufactured by Yunica Technical Research Institute) | 15.0% by weight |
| Softener: AQ-66 (under trade name; manufactured by Shichifuku Chemicals) | 3.5% by weight |
| Water | 55.5% by weight |
| Initial pH: 6.5 | |

Step 4

The temperature of the process bath with the dispersion solution poured therein is raised at a rate of 1° C./min to 50° C.; by retaining the temperature at 50° C., absolute absorption process is effected for 30 minutes.

COMPARATIVE EXAMPLE 1

Comparative Example 1 is a general type of panty stocking, which is prepared by adding only chitosan and a softener at the step 2 of Example 1.

Step 2

The dispersion solution is adjusted to satisfy the following conditions.

| | |
|---|---:|
| Chitosan: K-5 (under trade name; manufactured by Kurashiki Boseki) | 8.0% by weight |
| Softener: AQ-66 (under trade name; manufactured by Shichifuku Chemicals) | 4.0% by weight |
| Water | 88.0% by weight |
| Initial pH: 7.0. | |

COMPARATIVE EXAMPLE 2

Comparative Example 2 is a type of panty stocking recovered by the modification of the step 2 of Example 3 in such a way that no chitosan was used.

Step 2

The dispersion solution is adjusted to satisfy the following conditions.

| | |
|---|---:|
| Microcapsule containing and sealing therein α-hydroxy acids as the principal ingredient | 5.0% by weight |
| Microcapsule containing and sealing therein the moisturizing agent | 1.0% by weight |
| Softener: AQ-66 (under trade name; manufactured by Shichifuku Chemicals) | 3.5% by weight |
| Binder: NF-168N (under trade name; Yunica Technical Research Institute) | 15.0% by weight |
| Water | 75.5% by weight |
| Initial pH: 6.5. | |

Furthermore, Table 1 below collectively shows the experimental conditions of Examples 1 to 3 and Comparative Examples 1 and 2.

TABLE 1

| | | Example 1 | Example 2 | Example 3 | Comparative Example 1 | Comparative Example 2 |
|---|---|---|---|---|---|---|
| Microcapsule | α-hydroxy acid | 4.0% by weight | 5.0% by weight | 5.0% by weight | — | 5.0% by weight |
| | moisturizing agent | — | — | 1.0% by weight | — | 1.0% by weight |
| Chitosan | K-6 (Kurashiki Boseki) | 8.0% by weight | 10.0% by weight | — | 8.0% by weight | — |
| | SOK(Shichifuku Chemicals) | — | 5.0% by weight | 20.0% by weight | — | — |
| Binder | | — | — | 15.0% by weight | — | 15.0% by weight |
| Softener | | 4.0% by weight | 4.0% by weight | 3.5% by weight | 4.0% by weight | 3.5% by weight |
| Absolute absorption | upper limit of raised temp. | 40° C. | 50° C. | 50° C. | 40° C. | 50° C. |
| | initial pH | 7.0 | 6.8 | 6.5 | 7.0 | 6.5 |

The evaluation test carried out by using the panty stockings recovered in Examples 1 to 3 and Comparative Examples 1 and 2 is described below.

Evaluation of the Effect of Chitosan on Absolute Absorption

The evaluation of chitosan added to the dispersion solution as to the level of the effect on the absorption of the microcapsule was carried out, by using Example 3 and Comparative Example 2 recovered under conditions only differing in terms of the addition or non-addition of chitosan and comparing the color of the dispersion solution after absolute absorption process. Furthermore, the color of the dispersion solution at the microcapsule-floating state is opaque.

As shown in Table 2 below, the dispersion solution after absolute absorption was colorless and transparent in Example 3 with addition of chitosan. Thus, it was confirmed that the microcapsule was almost completely absorbed. In Comparative Example 2, alternatively, the dispersion solution after absolute absorption was opaque. Hence, it was confirmed that the microcapsule still remained when the binder was simply added. In Examples 1 and 2, the dispersion solution after absolute absorption process was colorless and transparent.

TABLE 2

| | Color of dispersion solution after absolute absorption process |
|---|---|
| Example 1 | colorless and transparent |
| Example 2 | colorless and transparent |
| Example 3 | colorless and transparent |
| Comparative Example 2 | opaque |

So as to enhance the absolute absorption effect, furthermore, the initial pH of the dispersion solution is particularly preferably within a range of 6.4 to 6.6. At the initial pH within the range, the color of the dispersion solution turned pale around 46° C. when the temperature was raised at a rate of 1° C./min up to 50° C., as shown above in Example 3; and the absolute absorption process could be completed most efficiently in about 30 minutes after the temperature reached 50° C.

Figure 3:
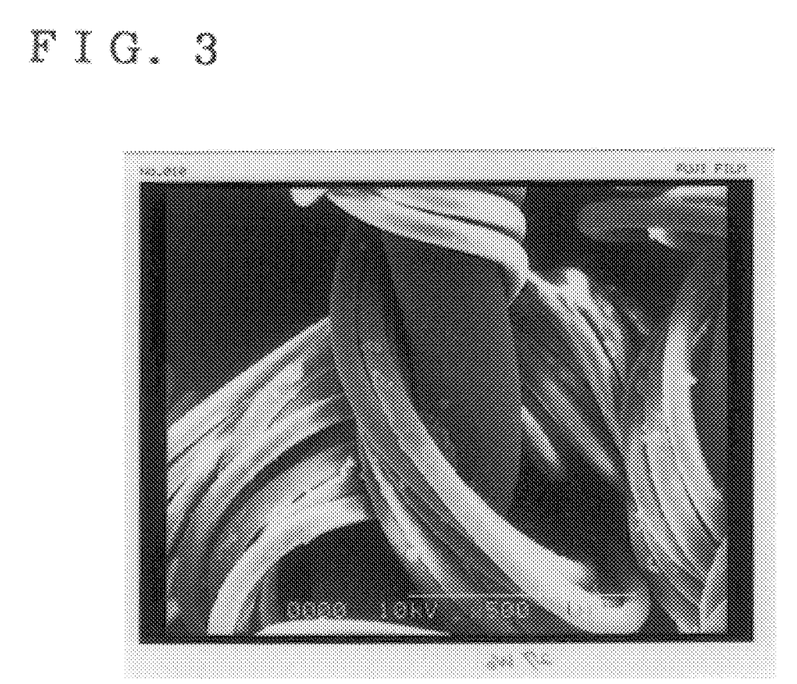
FIG. 3 shows a microscopic photograph (magnification: ×500), by which the attachment status of the microcapsule to the fiber of the panty stocking of Example 1 is confirmed.

FIG. 3 shows the results of the electromicroscopic observation (magnification: ×500) of the leg part of the panty stocking of Example 1, so as to confirm the status of the microcapsule attached to the panty stocking. The appearance of the microcapsule attached to the fiber is confirmed.

Evaluation of the Effect of α-Hydroxy Acids on the Improvement of Skin State

The effect of α-hydroxy acids on the improvement of skin dryness, skin roughness and wrinkle was evaluated by comparing Example 1 and Comparative Example 1, which differ in terms of only one condition, namely the addition or non-addition of the microcapsule containing and sealing therein α-hydroxy acids.

The test method is as follows; the panty stockings of Comparative Example 1 and Example 1 were worn by two test subjects for 30 days; what type of difference emerging on the skin states on their thighs was confirmed with a microscope (magnification; ×30), and the effect was evaluated.

Figure 2:
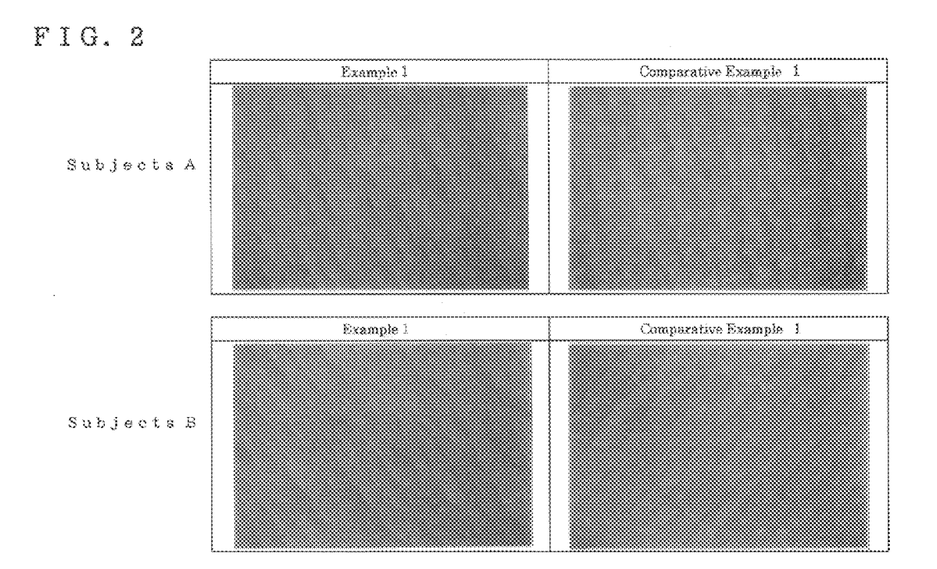
FIG. 2 shows microscopic photographs (magnification: ×30) comparatively depicting the skin states on sural regions, after the panty stockings of Example 1 and Comparative Example 1 are worn thereon.

As shown in the microscopic photographs in FIG. 2, consequently, no change was observed in the test subjects A and B putting on the panty stocking of Comparative Example 1. When they wore the panty stocking of Example 1, it was confirmed that the dry skin of the test subject A could retain appropriate moisture so the rough texture of the skin was finely improved and that the dry skin of the test subject B was more or less moistened so the texture of the skin was under way of improvement.

Furthermore, monitors wore the panty stocking of Example 3, for the comparison of the wear state with the wear state of the panty stocking of Comparative Example 1. The evaluation method comprised collecting the replicas of the skin surface morphology and visually observing the replicas, and performing a survey with questionnaire among the monitors. Additionally, the replicas were collected from their sural regions, thighs and ankles.

Figure 4:
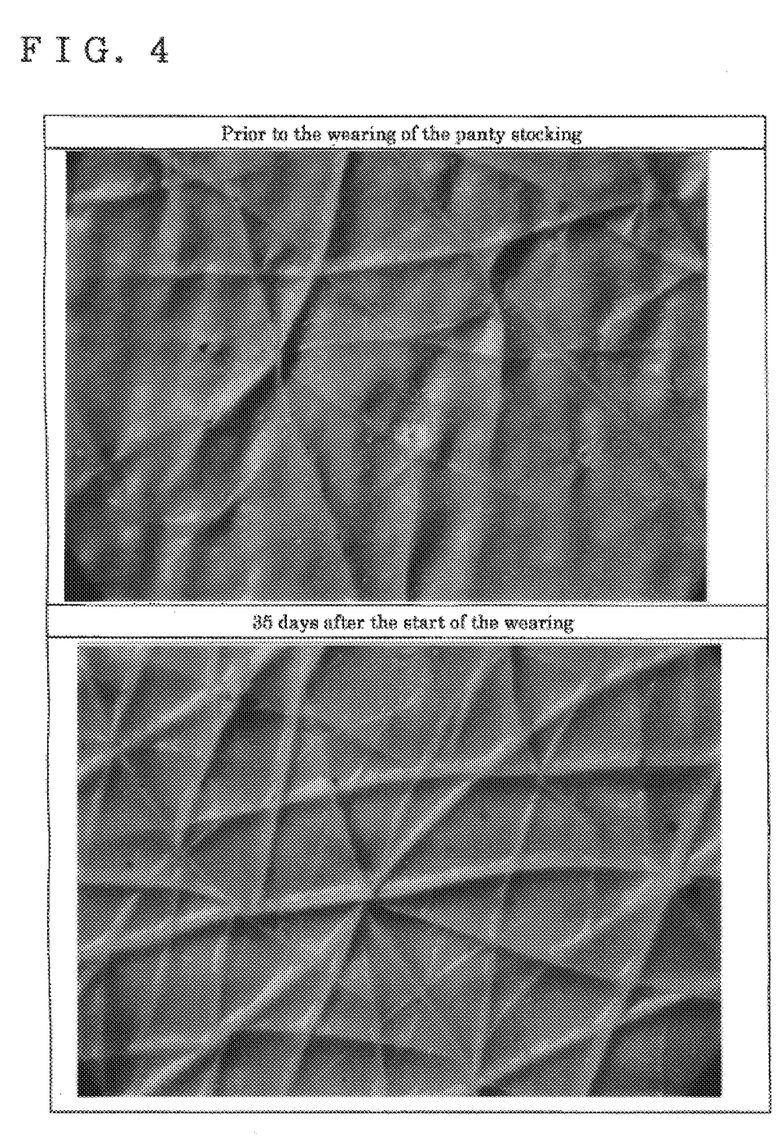
FIG. 4 shows enlarged replica photographs (magnification: ×40) comparatively depicting the skin states of sural region, prior to the wearing of the panty stocking of Example 3 and 35 days after the start of the wearing.

The results of the observation of the replicas over time revealed that no change was observed when the panty stocking of Comparative Example 1 was worn. Alternatively, it was confirmed that the skin pattern was more apparent, involving distinct skin groove and skin pubis in those wearing the panty stocking of Example 3 about 30 to 35 days after they started to wear the panty stocking of Example 3, indicating that the skin texture was finely improved. FIG. 4 shows enlarged replica photographs (magnification: ×40) of a certain monitor wearing the panty stocking of Example 3. It was confirmed that the skin pattern was prominent 35 days after the start of wearing. Such effect of the improvement could be confirmed at about 90% of the monitors enrolled in the test.

Additionally, it was confirmed from the results of the visual observation that the skin after the use of the panty stocking of Example 3 was rather at a better state with moisture and smoothness. Furthermore, the moisture, moistened state and smoothness of skin could be verified, on the basis of the results of the questionnaire among the monitors. Based on the replicas, no change was observed on the ankles. However, the effects of moisture and wet touch with no dryness were observed on the ankles.

Evaluation of Washing Durability

Using the panty stockings recovered in Examples 1 to 3, the test of washing durability was conducted. The test method is described below.

Water (30 liters) and a detergent (10 g) are placed in a washing machine, for 15-min washing. Then, 2-min dehydration, 5-min rinsing under water supply, 2-min dehydration, 5-min rinsing under water supply and 3-min rinsing are sequentially conducted in a series. As to the dry method, hang-out drying at a state under no direct influence of sunlight is conducted. The detergent was commercially available one, namely Attack (under trade name; manufactured by Kao, Co.).

Evaluation was conducted as follows: the status of the microcapsule attached to the fiber was observed with a microscope (magnification; ×750); and then, the status was ranked and assigned with the following 5 scores, for comparison.

5: enormous volume attached
4: considerable volume attached (75% or more of the volume with score 5 being attached)
3: attached (50% or more of the volume with score 5 being attached)
2: slight volume attached (35% or more of the volume with score 5 being attached)
1: more or less volume attached (15% or more of the volume with score 5 being attached)
almost no volume attached (less than 15% of the volume with score 5 being attached).

As shown below in Table 3, it was confirmed that washing durability was the highest in Example 3 with addition of the urethane-based resin binder. In Table 3, Wn means the results of observation after the n-th washing.

TABLE 3

| | Washing durability | | | | | | | | | | |
|---|---|---|---|---|---|---|---|---|---|---|---|
| | W0 | W1 | W2 | W3 | W4 | W5 | W6 | W7 | W8 | W9 | W10 |
| Example 1 | 3 | 3–2 | 3–2 | 2 | 2 | 1 | — | — | — | — | — |
| Example 2 | 4 | 3 | 4–3 | 2 | 2 | 2 | — | — | — | — | — |
| Example 3 | 5 | 5 | 5 | 5 | 5 | 5 | 5 | 5 | 5–4 | 4 | 4 |

Evaluation of Antibacterial Performance

Antibacterial performance test was subsequently conducted by using the panty stockings of Examples 1 to 3 and Comparative Example 2. By determining the viable cell number and calculating the bacterial reduction ratio by the shake-flask method, the evaluation was carried out.

As shown below in Table 4, both the viable cell number and bacterial reduction ratio were apparently better in Example 1 with addition of chitosan as crosslinking agent, than those in Comparative Example 2. Additionally, it was confirmed that the viable cell number and the bacterial reduction ratio were far better in Examples 2 and 3 with addition of more quantities of chitosan.

TABLE 4

Antibacterial performance

| | viable cell number | bacterial reduction ratio (%) |
|---|---|---|
| Example 1 | $1 \times 10^3$ | 99.5 |
| Example 2 | 0 | 99.9 or more |
| Example 3 | $1 \times 10^3$ | 99.5 |
| Comparative Example 2 | $1 \times 10^5$ | 3.9 |

As has been described above, the method for attaching the microcapsule in accordance with the invention can improve the absorption ratio of the microcapsule as much as possible during absorption reaction, owing to the addition of chitosan as crosslinking agent so that the amount of the microcapsule attached to fiber can be retained constant. Thus, the method can overcome the conventional problems from the respect of quality control. Additionally, the clothing promoting the metabolism of keratin layer in accordance with the invention can bring about effects on the reduction of skin dryness, skin roughness, wrinkle and spot, by promoting the metabolism of keratin layer through the attachment of the microcapsule with chitosan as crosslinking agent.

Furthermore, because the α-hydroxy acids contained and sealed are released at a constant rate from the clothing recovered by preparing the wall material of the microcapsule with an inorganic porous material in accordance with the invention, the action of α-hydroxy acids can continuously be exerted more effectively; and because the microcapsule is a sustained-release type with no occurrence of decomposition, the clothing can overcome the quality-control problem, namely microcapsule decomposition accompanied by the reduction of the effective microcapsule in volume prior to product shipment.

Additionally, the clothing given with the urethane-based resin binder so as to enhance the binding between the microcapsule and the fiber in accordance with the invention can get improved washing durability. Still furthermore, the clothing with a moisturizing agent used concurrently therein can retain the moisture content of skin at a preferable state, along with the action thereof for promoting the metabolism of keratin layer. Thus, the effect thereof on the resumption of skin moisture and softness once reduced can be enhanced.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A clothing comprising:

a fiber having a microcapsule containing and sealing therein at least about 10% by weight of at least one α-hydroxy acid, using chitosan as a crosslinking agent thereby improving the state of bare skin through the promotion of the metabolism of keratin layer;

said microcapsule and said chitosan being present within a range of from about 4:1 to about 1:6 in weight ratio; and a total amount of said microcapsule and said chitosan occupying from about 0.1 to about 15% of the fiber weight at a dry state.

2. A clothing according to claim 1, wherein a wall material of said microcapsule comprises an inorganic porous material.

3. A clothing according to claim 1, further comprising:

an urethane-based resin binder for enhancing binding between said microcapsule and said fiber;

said microcapsule and said urethane-based resin binder being at a weight ratio within a range of from about 4:1 to about 1:5.

4. A clothing according to claim 1, wherein:

said clothing is prepared by attaching to said fiber said microcapsule containing and sealing therein at least one moisturizing agent selected from the group consisting of cucumber extract, squalene, mugwort extract and trehalose;

said microcapsule further including said α-hydroxy acids; and a ratio of α-hydroxy acids to said moisturizing agents is within a range of from about 4:1 to about 1:3.

5. A clothing according to claim 1, wherein the clothing is stockings.

6. A method for attaching a microcapsule to a fiber, comprising:

forming a dispersion solution containing from about 4 to about 20% by weight of said microcapsule and at least 4 to about 30% by weight of chitosan;

adjusting an initial pH of said dispersion within a range of from about 6.0 to about 7.0;

immersing said fabric into a process bath;

pouring said dispersion in said process bath;

adjusting the temperature of said process bath charged with said dispersion solution up to a range from about 40 to about 55° C.; and maintaining said temperature to carry out absolute absorption of said microcapsule onto said fiber.

* * * * *